(12) United States Patent
Attinger

(10) Patent No.: US 11,019,990 B2
(45) Date of Patent: Jun. 1, 2021

(54) LARYNGOSCOPE AND BLADE A FOR A LARYNGOSCOPE

(71) Applicant: KARL STORZ SE & Co. KG, Tuttlingen (DE)

(72) Inventor: Jürg Attinger, Stein am Rhein (CH)

(73) Assignee: KARL STORZ SE & Co. KG, Tuttlingen (DE)

( * ) Notice: Subject to any disclaimer, the term of this patent is extended or adjusted under 35 U.S.C. 154(b) by 89 days.

(21) Appl. No.: 16/290,075

(22) Filed: Mar. 1, 2019

(65) Prior Publication Data

US 2019/0274533 A1  Sep. 12, 2019

(30) Foreign Application Priority Data

Mar. 9, 2018 (DE) ...................... 10 2018 105 538.2

(51) Int. Cl.
*A61B 1/267* (2006.01)
*A61B 1/00* (2006.01)

(52) U.S. Cl.
CPC ............ *A61B 1/267* (2013.01); *A61B 1/0008* (2013.01); *A61B 1/00071* (2013.01)

(58) Field of Classification Search
CPC ........... A61B 1/267; A61B 13/00; A61B 1/24; A61M 16/0495
See application file for complete search history.

(56) References Cited

U.S. PATENT DOCUMENTS

| 668,823 | A | * | 2/1901 | Pilling | ................... A61B 13/00 600/240 |
| 1,388,170 | A | | 8/1921 | Cameron | |
| 2,569,179 | A | | 9/1951 | Lanchart | |
| 3,568,680 | A | * | 3/1971 | Raimo | .............. A61M 16/0488 128/207.14 |
| 4,527,553 | A | * | 7/1985 | Upsher | .................... A61B 1/07 600/188 |
| 4,589,848 | A | * | 5/1986 | Inoue | ....................... A61C 5/90 433/140 |
| 5,178,132 | A | | 1/1993 | Mahefky | |
| 2007/0232862 | A1 | * | 10/2007 | Herman | ................. A61B 1/267 600/190 |
| 2010/0249513 | A1 | | 9/2010 | Tydlaska | |
| 2010/0298644 | A1 | * | 11/2010 | Kleene | ................. A61B 1/2676 600/188 |
| 2016/0213241 | A1 | | 7/2016 | Goldstein | |

FOREIGN PATENT DOCUMENTS

| DE | 10 2016 001 309 A1 | 8/2017 | |
| EP | 0030014 A1 * | 6/1981 | ............. A61B 1/267 |
| EP | 0 339 541 A1 | 11/1989 | |
| WO | 2007/087446 A2 | 8/2007 | |

\* cited by examiner

*Primary Examiner* — Julianna N Harvey
(74) *Attorney, Agent, or Firm* — McGlew and Tuttle, P.C.

(57) ABSTRACT

A blade (20) for a laryngoscope (10) includes a proximal end (24), which is mechanically connected or connectable to a handle (16), a distal end (22), and an opening (52) near the distal end (22) of the blade (20). The opening (52) is arranged and configured in such a way that a view can be obtained, through the opening (52), from the side (28) to be directed toward a patient's palate during the intended use of the blade (20) to the side (26) to be directed toward the base of the patient's tongue during the intended use of the blade (20).

20 Claims, 5 Drawing Sheets

22,32　52　56　54　30

22,32　52　56　54　30

22,32　52　56　54　30

LARYNGOSCOPE AND BLADE A FOR A LARYNGOSCOPE

CROSS REFERENCE TO RELATED APPLICATIONS

This application claims the benefit of priority under 35 U.S.C. § 119 of German Application 10 2018 105 538.2, filed Mar. 9, 2018, the entire contents of which are incorporated herein by reference.

TECHNICAL FIELD

The present invention relates to a blade for a laryngoscope and to a laryngoscope comprising such a blade.

TECHNICAL BACKGROUND

When performing (or, to be more precise, directly before performing) an endotracheal intubation, the epiglottis is generally lifted by means of a laryngoscope from the entrance to the larynx and is immobilized in the position in which it does not close the larynx. This requires precise positioning of the distal end of the laryngoscope on or under the epiglottis, which is made easier if the laryngoscope is equipped with an imaging device, in particular a camera, near its distal end. However, performing this procedure requires not only anatomical knowledge but also dexterity and experience. Generally, the laryngoscope is moved to and fro several times in an iterative approach until its distal end adopts a suitable position.

SUMMARY

An object of the present invention is to make available an improved blade for a laryngoscope and an improved laryngoscope.

A blade for a laryngoscope comprises a proximal end, which is mechanically connected or connectable to a handle, a distal end, and an opening near the distal end of the blade, wherein the opening is arranged and configured in such a way that a view can be obtained, through the opening, from the side to be directed toward a patient's palate during the intended use of the blade to the side to be directed toward the base of the patient's tongue during the intended use of the blade.

The blade is provided in particular for an intubation laryngoscope for anesthesia, emergence medicine or intensive care medicine, or for a laryngoscope for surgery of the larynx or for other purposes in otorhinolaryngology, or is part of such a laryngoscope. The blade may be likened, apart from the opening, to a conventional blade, for example the blades after Macintosh, Miller, Dörges or McCoy.

The proximal end of the blade can be mechanically connected or connectable to the handle either rigidly or in an articulated manner. The distal end of the blade is provided and designed to be introduced into the patient's throat during the intended use of the blade.

The blade can be provided and designed for use with an endoscope, in particular a flexible endoscope, or another device for capturing and reproducing an image of the environment of the distal end of the blade. Alternatively, the blade can have, near its distal end, a camera or an objective and a distal end of a coherent optical waveguide bundle or of a relay lens system or of another device for transmitting the image captured by the objective. Alternatively, the blade can be provided and designed to receive, near its distal end, a camera with an objective and with an image sensor. The distal end of the endoscope or the objective or the camera is in this case arranged at or near a side of the blade to be directed toward the patient's palate during the intended use of the blade and, without the opening, would not provide a view of the side to be directed toward the base of the patient's tongue during the intended use of the blade.

The opening facilitates a view of the side of the blade that is to be directed toward the base of the patient's tongue during the intended use of the blade. This may make correct positioning of the blade easier and may thus in particular facilitate a more rapid and more reliable endotracheal intubation. The possible view through the opening to the side to be directed toward the base of the patient's tongue during the intended use may also be advantageous for other applications.

In a blade as described here, the opening is in particular not closed by a component made of an optically transparent material.

A window component made of an optically transparent material may appear advantageous from the mechanical point of view. However, reflections occurring at the surfaces of such a window component (including total reflection at the transition from the transparent material to air) can make the construction of the window component considerably difficult and/or may make observation through the window component impossible. By contrast, the provision of a simple opening near the distal end of the blade facilitates a clear observation through the window, in a manner not adversely affected by reflections.

In a blade as described here, the opening has in particular a rectangular or substantially rectangular configuration.

The opening is rectangular or substantially rectangular when its area content is not less than four fifths or nine tenths or nineteen twentieths of the area content of a circumscribing rectangle. When the opening is bounded by edges with inclined flanks, the opening is rectangular or substantially rectangular in the above sense if the stated criterion is true for a section along a plane or a curved surface corresponding to the convexity of the blade.

In a blade as described here, the opening has in particular a circular or substantially circular or elliptical or substantially elliptical configuration.

The opening is circular or substantially circular or elliptical or substantially elliptical when its area content is not less than four fifths or nine tenths or nineteen twentieths of the area content of a circumscribing circle or a circumscribing ellipse.

In a blade as described here, the shape of the opening is adapted in particular to the typical shape of the human epiglottis.

If the blade is provided and designed for adult patients, the shape of the opening is adapted in particular to the typical shape of the epiglottis of a male or female adult patient. If the blade is provided and designed for infant or adolescent patients, the shape of the opening is adapted in particular to the typical shape of the epiglottis of an infant or adolescent patient. If the blade is provided and designed for patients with a predetermined body size or a predetermined size of the head or of the throat, the shape of the opening is adapted in particular to the typical shape of a male or female patient with the predetermined body size or the predetermined size of head or throat.

The adaptation of the shape of the opening to the typical shape of the human epiglottis can facilitate an adjustment, by form-fit engagement, of the positioning of the blade. This applies in particular when the blade is arranged posteriorly of the epiglottis in order to press the latter in the anterior direction.

A blade as described here, having a plurality of openings, moreover comprises in particular a web between two openings.

A plurality of openings of the blade are separated from one another in particular by one or more webs. The same overall situation can be described as being that an overall opening is divided into a plurality of part openings by one or more webs. The panel or the panels are arranged in particular like the panel or the panels of a panel window, although in contrast to a panel window no glass is provided in the openings.

One or more webs can prevent or reduce penetration or bulging of tissue surfaces into the opening without substantially limiting the view to the side of the blade that is to be directed toward the base of the tongue during the intended use of the blade. One or more webs can moreover increase the mechanical stability of the blade.

In a blade as described here, the web is in particular arranged parallel or substantially parallel to the longitudinal direction of the blade or orthogonal or substantially orthogonal to the longitudinal direction of the blade or at an angle, not less than 30 degrees and not more than 60 degrees, to the longitudinal direction of the blade.

A web is arranged parallel or substantially parallel to the longitudinal direction of the blade if the web encloses, with the longitudinal direction, an angle of not more than 10 degrees or not more than 20 degrees or not more than 30 degrees. The web is arranged orthogonally or substantially orthogonally to the longitudinal direction of the blade if the angle between the web and the longitudinal direction of the blade is not less than 60 degrees or not less than 70 degrees or not less than 80 degrees.

A blade as described here moreover comprises in particular a further web, which is arranged parallel to the web or intersects the web.

For example, two intersecting webs, of which one is arranged substantially parallel and the other substantially orthogonal to the longitudinal direction of the blade, can divide a substantially rectangular overall opening into four substantially rectangular part openings. Alternatively, for example, two substantially parallel webs can divide a substantially rectangular overall opening into three part openings.

A blade as described here moreover comprises in particular a net or lattice of a plurality of webs which intersect one another or whose ends are connected to one another.

The ends of three or four or more webs form a node. Three, four or more webs form a mesh of the net or lattice.

The net or lattice is in particular rigid, i.e. non-elastic. For this purpose, the webs are formed in particular from a rigid or non-elastic material, and their ends are rigidly connected to one another. Alternatively, the net or lattice can be elastic. For this purpose, the webs have in particular an elastic material and/or their ends are connected elastically to one another.

In a blade as described here, one or more or all of the openings have a substantially square or rectangular or rhombic or hexagonal shape or another polygonal shape.

In a blade as described here, the webs form in particular a honeycomb structure.

For this purpose, six straight or substantially straight webs enclose an opening or part opening, and interconnected ends of in each case three webs form a node.

In a blade as described here, in particular, a region of the blade or the entire blade is formed by webs, between which the opening or a plurality of openings are arranged.

With the webs arranged in a net shape or lattice shape, the openings are formed by the meshes of the net or lattice. If it is not the entire blade but only a region of the blade that is formed by webs, this region is in particular a distal region of the blade.

In a blade as described here, the region formed by webs is in particular at least either strip-shaped or rectangular.

The straight or substantially straight edge portions of the strip-shaped and/or rectangular region formed by webs are in particular parallel or orthogonal to the longitudinal direction of the blade.

In a blade as described here, the opening is arranged at least either distally in relation to a light exit face, through which illumination light exits during the intended use of the blade, or distally in relation to a light admission face, through which an image of the environment of the distal end of the blade can be captured during the intended use of the blade.

The light exit face is in particular a light exit face at a window component or optical waveguide or optical waveguide bundle connected permanently and rigidly to the blade. Alternatively, the light exit face can be a light exit face at a window component or optical waveguide or optical waveguide bundle not connected permanently to the blade, in a predetermined position. In this case, the predetermined position of the light exit face is in particular defined by form-fit engagement, for example by a mechanical limit stop which is as far as an illumination device with the light exit face can be moved distally relative to the blade, and which prevents a further movement in the distal direction.

The light admission face is in particular a light admission face at an objective or at a window component behind which a camera or an objective and an image sensor or an objective and a distal end of a coherent bundle of optical waveguides or of a relay lens system or of another image-transmitting device is arranged. The objective or the window component with the light admission face can be connected permanently to the blade, for example as part of a camera integrated in the blade or of an endoscope integrated in the blade or of another image-capturing device or image-transmitting device integrated in the blade. Alternatively, the light admission face can be provided at a camera or an endoscope or another image-capturing device or image-transmitting device which is not mechanically connected permanently to the blade but instead can be combined with the blade and is mechanically connectable thereto. The predetermined position of the light admission face is in particular defined by a form-fit engagement, for example by a mechanical limit stop which is as far as the camera or the endoscope or the image-transmitting device or the image-capturing device with the light admission face can be moved distally relative to the blade, and which prevents a further movement in the distal direction.

A laryngoscope comprises a blade, as described here, and a handle which is connected or connectable to the proximal end of the blade.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
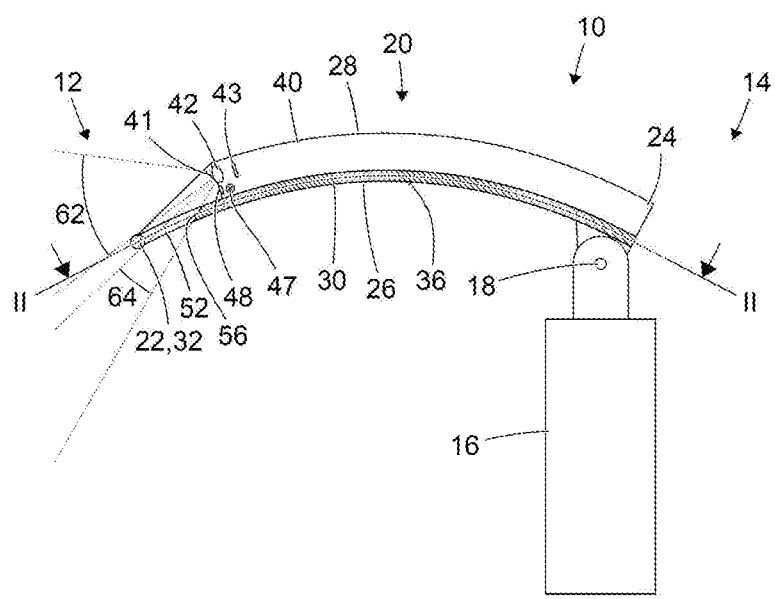
FIG. 1 is a schematic view of a laryngoscope.

Referring to the drawings, FIG. 1 shows a schematic view of a laryngoscope 10 which, for example, is suitable for aiding endotracheal intubation. The laryngoscope 10 has a distal end 12, which is provided and designed to be introduced into a patient's throat. The laryngoscope 10 moreover has a proximal end 14, which is formed substantially by a handle 16. The handle 16 is connected to a curved blade 20, by a lockable joint 18 in the example shown. A distal end 22 of the blade 20 forms the distal end 12 of the laryngoscope 10. A proximal end 24 of the blade 20 is connected to the handle 16 by said joint 18. Alternatively, the proximal end 24 of the blade 20 can be connected to the handle 16 in a mechanically rigid manner, either permanently or releasably.

The blade 20 has a side 26 to be directed toward a patient's tongue during the intended use of the laryngoscope 10 and, facing away from the side 26, a side 28 to be directed toward a patient's palate during the intended use. The side 26 of the blade 20, to be directed toward a patient's tongue, is formed by a beam-shaped structure 30. At its distal end, the beam-shaped structure has a thickened portion 32, which forms the distal end 22 of the blade 20. The thickened portion 32 facilitates or supports an atraumatic use of the laryngoscope 10 with the greatest possible radii of curvature.

Cross sections of the beam-shaped structure 30 in planes orthogonal to the drawing plane of FIG. 1 are, excepting the thickened portion 32 at its distal end and excepting features described below, substantially rectangular with rounded corners. The beam-shaped structure 30 is curved in accordance with the curvature of the whole blade 20. At the side 26 of the blade 20 to be directed toward a patient's tongue, the beam-shaped structure 30 has a surface region 36 intended to rest on the patient's tongue.

The blade 20 moreover comprises a hollow body 40 which extends from the proximal end 24 over much of the length of the blade 20, as far as a location at a predetermined distance from the distal end 22 of the blade 20. While the beam-shaped structure 30 forms the side 26 of the blade 20 to be directed toward a patient's tongue, the hollow body 40 forms the side 28 of the blade 20 to be directed toward the patient's palate. The hollow body 40 does not occupy the entire width of the blade 20 but instead, viewed from the proximal direction, only the right-hand side for example, such that the beam-shaped structure 30 protrudes at the left-hand side directed toward the person looking at the view in FIG. 1.

In the view in FIG. 1, the beam-shaped structure 30 is shown in a section along a plane lying outside the hollow body 40. The hollow body 40 is thus shown in a plan view. However, a light admission face 41 of the blade 20, an objective 42, and an image sensor 43 proximally of the objective 42 are indicated at the distal end of the hollow body 40, even though at least the objective 42 lies for the most part, and the image sensor 43 completely, inside the hollow body 40, such that they are therefore not visible from the viewing direction shown in FIG. 1. In the example shown, the light admission face 41 of the blade 20 is formed by a light admission face of the objective 42.

The objective 42 and the image sensor 43 form a camera integrated in the laryngoscope 10 and constitute an example of an image-capturing device for capturing an image of the environment of the distal end 22 of the blade 20. This image-capturing device can, instead of the image sensor 43, have a distal end of a coherent bundle of optical fibers, of a relay lens system or of another device for transmitting the image generated by the objective 42 to the proximal end 14 of the laryngoscope 10.

The camera or the other image-capturing device for capturing an image of the environment of the distal end 22 of the blade 20 can be mechanically connected to the blade 20 permanently and in a manner that is not readily releasable. Alternatively, the camera or the other image-capturing device can be connected releasably to the blade 20, for example by being pushed into the hollow body 40 from the proximal direction as far as a limit stop. The light admission face 41 can in this case be a light admission face of a window component that closes the hollow body 40 in a fluid-tight manner or hermetically at the distal end. Alternatively, the light admission face 41 is the light admission face of the camera or of the other image-capturing device. In the latter case, the position of the light admission face 41 relative to the blade 20 and to the distal end 22 thereof is defined in particular by the intended design of the camera or of the other image-capturing device, and by the position and orientation, defined for example by form-fit engagement, of the camera or of the other image-capturing device relative to the blade 20.

Although, as has been mentioned, the hollow body 40 in FIG. 1 is not shown in section, a light source 47 and a light exit face 48 are moreover indicated at the distal end of the hollow body 40. The light source 47 comprises, for example, one or more light-emitting diodes. Illumination light generated by the light source 47 leaves the blade through the light exit face 48 and illuminates the environment of the distal end 22 of the blade 20. In order to prevent or minimize shading by the distal end 22 of the blade 20, the light exit face 48 can partially or completely surround the light admission face 41, or a plurality of light exit faces can be provided which can in particular be arranged at opposite sides of the light admission face 41.

Near its distal end 22, the blade 20 has an opening 52 in the beam-shaped structure 30. The opening 52 facilitates viewing or observation, by means of the objective 42 and of the image sensor 43, not only of a viewing field 62, but also of a wider viewing field 64 at the side 26 of the blade 20 to be directed toward a patient's tongue. This can make the correct positioning of the distal end 22 of the blade 20 much easier.

The proximal edge portion of the opening 52 in the beam-shaped structure 30 has an inclined flank 56. This inclination facilitates a particularly favorable ratio between the size of the surface region 36 of the beam-shaped structure 30, provided to rest on a patient's tongue, and the size of the second viewing field 64.

The opening 52 is in particular not closed by a window component of a transparent material, such that neither reflections nor solid or liquid deposits at the surfaces of such a window component can obstruct the view through the opening 52.

Figure 2:
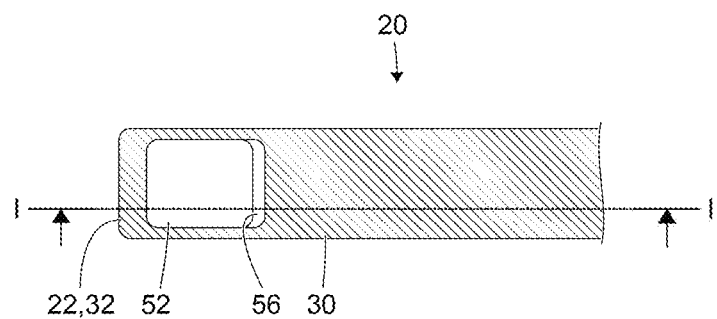
FIG. 2 is a schematic view of a section through a blade of the laryngoscope from FIG. 1.

FIG. 2 shows an enlarged schematic view of a section along the curved surface II-II indicated in FIG. 1 and following the shape of the beam-shaped structure 30. The position of the section plane I-I, in which the beam-shaped structure 30 is shown in FIG. 1, is indicated in FIG. 2.

The elongate and rectangular basic configuration of the beam-shaped structure can be seen in FIG. 2. As has already been mentioned, the cross section of the beam-shaped structure 30 in a plane orthogonal to the drawing plane in FIG. 1 and to the section face II-II of FIG. 2 is in particular a flat rectangle with rounded corners. The corners shown in FIG. 2 at the distal end 32 of the beam-shaped structure 30 and thus at the distal end 22 of the blade 22 are also rounded.

In the example shown, the opening 52 in the beam-shaped structure 30 of the blade 20 is likewise substantially rectangular with rounded corners. As has been mentioned, the inclined flank 56 of the proximal straight edge portion is inclined with respect to the section face II-II shown in FIG. 2.

Figure 3:
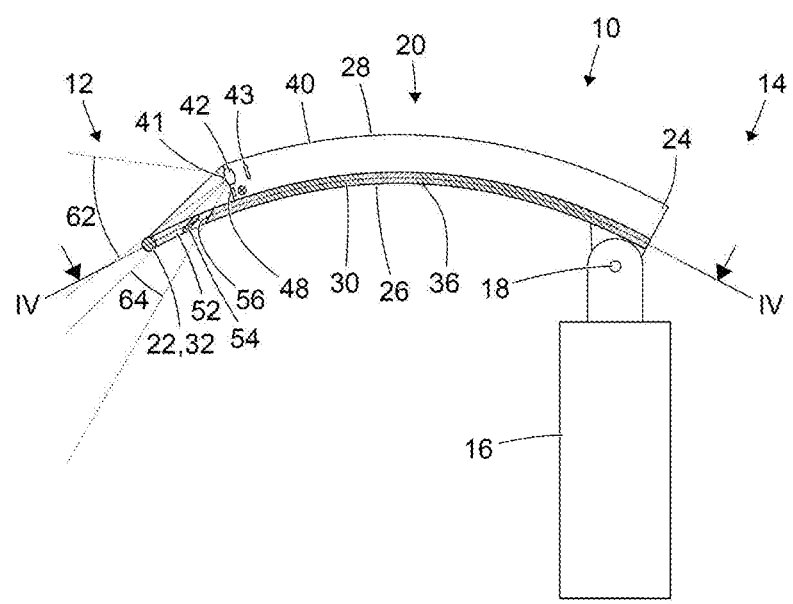
FIG. 3 is a schematic view of a further laryngoscope.

FIG. 3 shows a schematic view of a further laryngoscope 10 which, in terms of certain features, properties and functions, is similar to the laryngoscope shown in FIGS. 1 and 2. The view shown in FIG. 3 corresponds in nature to the view shown in FIG. 1. Features, properties and functions of the laryngoscope 10 shown in FIG. 3 that distinguish it from the laryngoscope shown in FIGS. 1 and 2 are described below in particular.

The laryngoscope 10 shown in FIG. 3 differs from the laryngoscope shown in FIGS. 1 and 2 particularly in that the opening 52 near the distal end 22 of the blade 20 is divided by a web 54 into a plurality of part openings.

Figure 4:
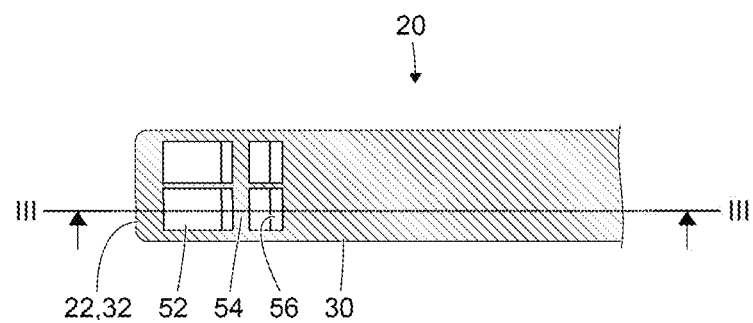
FIG. 4 is a schematic view of a section through a blade of the laryngoscope from FIG. 3.

FIG. 4 is a schematic view of a section through the beam-shaped structure 30 of the blade 20 of the laryngoscope 10 shown in FIG. 3, along the curved section face IV-IV indicated in FIG. 3 and following the configuration of the beam-shaped structure 30. The position of the section plane III-III, in which the beam-shaped structure 30 is shown in FIG. 3, is indicated in FIG. 4.

It will be seen in FIG. 4 that two webs 54 intersecting each other and thus passing through each other divide the opening 52 in the blade 20 into four part openings. An alternative way of describing the resulting structure is that the blade 20, namely the beam-shaped structure 30 thereof, has a plurality of openings 52 that are separated from one another by webs 54.

The structure shown in FIG. 4 can be described as being that a web 54 arranged in the longitudinal direction (horizontally in FIG. 4) and a web arranged in the transverse direction (vertically in FIG. 4) intersect or pass through one another. An alternative way of describing the structure shown in FIG. 4 is that a respective end of two webs arranged in the longitudinal direction of the blade 20 and a respective end of two webs arranged in the transverse direction form a node. The outer edges of the beam-shaped structure 30, to the sides of (below or above in FIG. 3) the openings 52, and the distal edge (left-hand edge in FIG. 4) of the beam-shaped structure 30 can also be described as webs. In this description, the entire distal (left-hand side in FIG. 4) edge region of the beam-shaped structure 30 is composed of a net or lattice of a plurality of webs 54 which intersect one another or whose ends are connected mechanically rigidly to one another.

Figure 5:
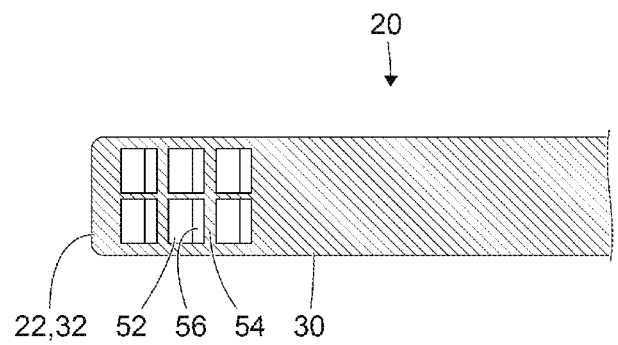
FIG. 5 is a schematic view of a section through a further blade.

FIG. 5 shows a schematic view of a further alternative embodiment of a blade 20 of a laryngoscope with features, properties and functions which are similar to or may be likened to the features, properties and functions of the laryngoscopes shown in FIGS. 1 to 4. The view shown in FIG. 5 corresponds in nature to the views shown in FIGS. 2 and 4. It thus shows a section through a curved beam-shaped structure 30 of the blade 20 along a surface that follows the curved beam-shaped structure 30. Features, properties and functions of the blade 20 that distinguish it from the blades shown in FIGS. 1 to 4 are described below in particular.

In the blade 20 shown in FIG. 5, the beam-shaped structure 30 has a larger number of openings or part openings 52, which are separated from one another by a net or lattice of webs 54. Two transverse webs and one longitudinal web, which intersect or pass through one another, divide a total of six openings or part openings 52 from one another, of which in each case two are arranged alongside each other and in each case three are arranged behind one another.

Figure 6:
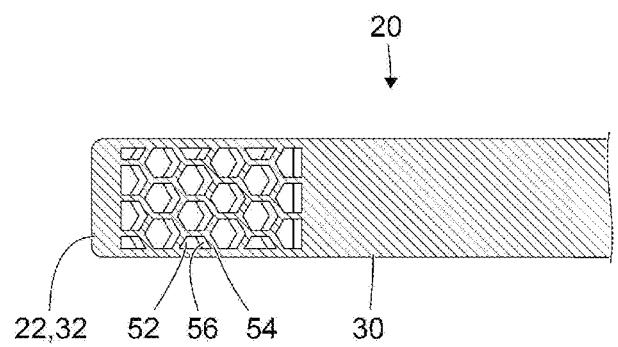
FIG. 6 is a schematic view of a section through a further blade.

FIG. 6 shows a schematic view of a further alternative embodiment of a blade 20 of a laryngoscope with features, properties and functions which are similar to or may be likened to the features, properties and functions of the laryngoscopes shown in FIGS. 1 to 5. The view shown in FIG. 5 corresponds in nature to the views shown in FIGS. 2, 4 and 5. It thus shows a section through a beam-shaped structure 30 of the blade 20 along a surface that follows the curved beam-shaped structure 30. Features, properties and functions of the blade 20 that distinguish it from the blades shown in FIGS. 1 to 5 are described below in particular.

In the example shown in FIG. 6, the webs 54 form a hexagonal lattice, similar to a honeycomb structure produced by bees. The openings or part openings 52 separated from one another by the webs 54, and not lying at the edge, are in each case hexagonal.

Figure 7:
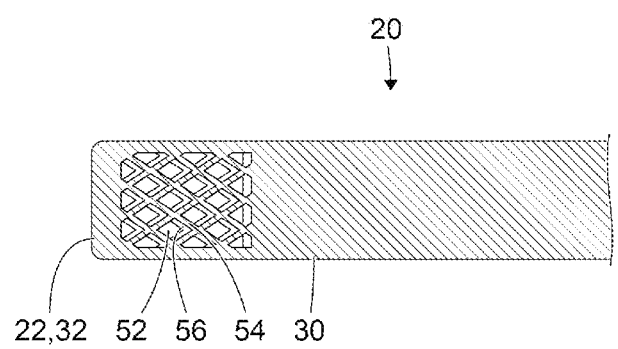
FIG. 7 is a schematic view of a section through a further blade.

FIG. 7 shows a schematic view of a further alternative embodiment of a blade 20 of a laryngoscope with features, properties and functions which are similar to or may be likened to the features, properties and functions of the laryngoscopes shown in FIGS. 1 to 6. The view shown in FIG. 7 corresponds in nature to the views shown in FIGS. 2 and 4 to 6. It thus shows a section through a beam-shaped structure 30 of the blade 20 along a surface that follows the curved beam-shaped structure 30. Features, properties and functions of the blade 20 that distinguish it from the blades shown in FIGS. 1 to 4 are described below in particular.

In the example shown in FIG. 7, the webs 54 form a rhombic lattice. The openings or part openings 52 separated from one another by the webs 54, and not lying at the edge, each have a substantially rhombic or diamond-shaped configuration.

Figure 8:
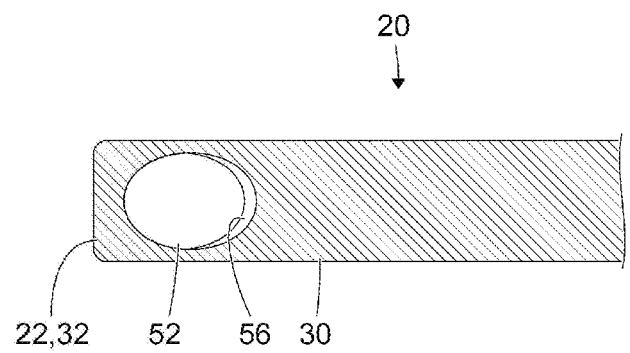
FIG. 8 is a schematic view of a section through a further blade.

FIG. 8 shows a schematic view of a further alternative embodiment of a blade 20 of a laryngoscope with features, properties and functions which are similar to or may be likened to the features, properties and functions of the laryngoscopes shown in FIGS. 1 to 7. The view shown in FIG. 8 corresponds in nature to the views shown in FIGS. 2 and 4 to 7. It thus shows a section through a beam-shaped structure 30 of the blade 20 along a surface that follows the curved beam-shaped structure 30. Features, properties and functions of the blade 20 that distinguish it from the blades shown in FIGS. 1 to 7 are described below in particular.

In the example shown in FIG. 8, the blade 20 has a single elliptical opening 52 in the beam-shaped structure 30.

Figure 9:
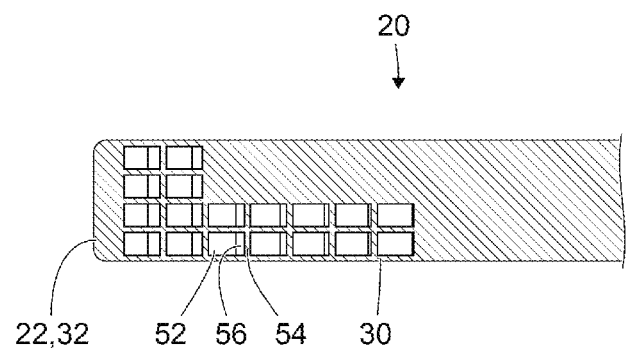
FIG. 9 is a schematic view of a section through a further blade.

FIG. 9 shows a schematic view of a further alternative embodiment of a blade 20 of a laryngoscope with features, properties and functions which are similar to or may be likened to the features, properties and functions of the laryngoscopes shown in FIGS. 1 to 8. The view shown in FIG. 9 corresponds in nature to the views shown in FIGS. 2 and 4 to 8. It thus shows a section through a beam-shaped structure 30 of the blade 20 along a surface that follows the curved beam-shaped structure 30. Features, properties and functions of the blade 20 that distinguish it from the blades shown in FIGS. 1 to 8 are described below in particular.

In the example shown in FIG. 9, the blade 20, similarly to the examples shown in FIGS. 4 and 5, has a plurality of in each case substantially rectangular openings or part openings 52 which, taken together, occupy an L-shaped region of the blade 20. One limb of the L-shaped region occupied by the openings or part openings 52 is arranged distally in relation to the distal end of the hollow body 40 (not shown in FIGS. 2 and 4 to 9) and therefore distally in relation to the light admission face 41 and the light exit face 48 (cf. FIGS. 1 and 2). This limb of the L-shaped region extends over the entire width or substantially over the entire width of the blade 20. The other limb of the L-shaped region in which the openings or part openings 52 are arranged extends at least partially alongside the hollow body 40 (not shown in FIGS. 2 and 4 to 9) of the blade 20 (cf. FIGS. 1 and 2) and, for example in the case of an endoscope introduced alongside the hollow body into a patient's throat, can facilitate a view, through said endoscope, of the tongue or the base of the tongue of the patient.

In the example shown in FIG. 9, the flanks 56 of the edges of the openings or part openings 52 have different inclinations. The flanks of proximal openings are steep, and the flanks have a continuously greater inclination in the distal direction. This may improve the view through the openings or part openings 52 and/or increase the mechanical stability of the webs 54. Differently inclined flanks 56 of this kind can also be provided in the blades shown in FIGS. 4 to 7.

Figure 10:
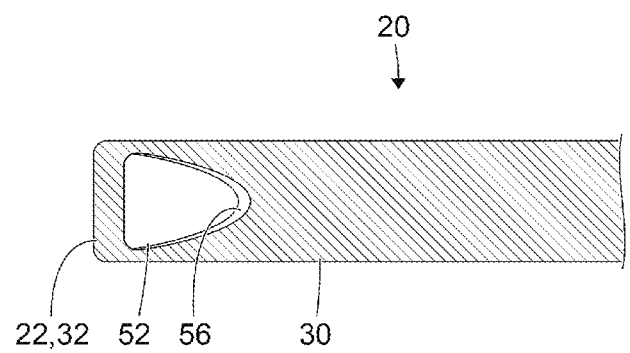
FIG. 10 is a schematic view of a section through a further blade.
Figure 11:
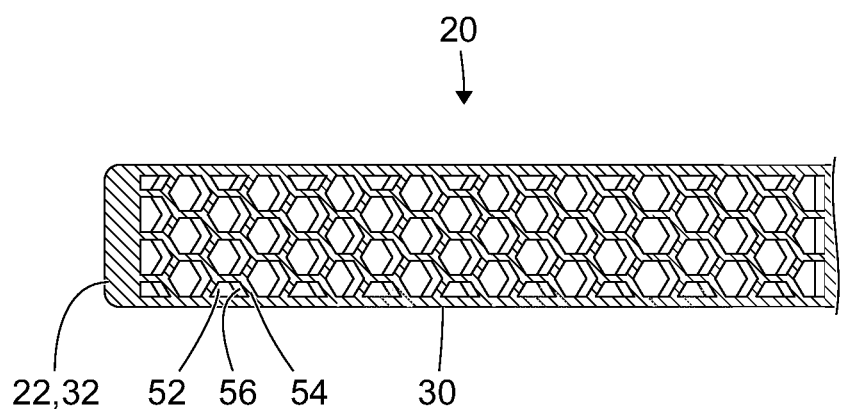
FIG. 11 is a schematic view showing the entire blade formed by webs.

FIG. 10 shows a schematic view of a further alternative embodiment of a blade 20 of a laryngoscope with features, properties and functions which are similar to or may be likened to the features, properties and functions of the laryngoscopes shown in FIGS. 1 to 9. The view shown in FIG. 10 corresponds in nature to the views shown in FIGS. 2 and 4 to 9. It thus shows a section through a beam-shaped structure 30 of the blade 20 along a surface that follows the curved beam-shaped structure 30. Features, properties and functions of the blade 20 that distinguish it from the blades shown in FIGS. 1 to 9 are described below in particular.

In the example shown in FIG. 10, the blade 20, similarly to the examples shown in FIGS. 2 and 8, has only a single large opening 52. In contrast to the blades shown in FIGS. 2 and 8, the shape of the opening 52 in the blade 20 shown in FIG. 10 is adapted approximately to the shape of the human epiglottis. This may facilitate a partial engagement of the epiglottis in the opening 52, and thus a form-fit connection between the blade 20 and the epiglottis, and may in turn make it easier to position the blade 20.

While specific embodiments of the invention have been shown and described in detail to illustrate the application of the principles of the invention, it will be understood that the invention may be embodied otherwise without departing from such principles.

The invention claimed is:

1. A blade for a laryngoscope, the blade comprising:
a proximal end mechanically connected or connectable to a handle;
a distal end; and
an opening near the distal end of the blade, wherein the opening is arranged and configured in such a way that a view can be obtained, through the opening, from a palate side to be directed toward a patient's palate during an intended use of the blade to a tongue side to be directed toward a base of the patient's tongue during the intended use of the blade, said opening having an inclined flank, the opening being arranged at least either distally in relation to a light exit face, through which illumination light exits during the intended use of the blade, or distally in relation to a light admission face, through which an image of the environment of the distal end of the blade can be captured during the intended use of the blade.

2. A blade according to claim 1, wherein the opening is not closed by a component made of an optically transparent material.

3. A blade according to claim 1, wherein a shape of the opening is adapted to the typical shape of the human epiglottis.

4. A blade according to claim 1, further comprising:
at least another opening to provide a plurality of openings; and
a web between two openings of the plurality of openings.

5. A blade according to claim 4, further comprising: a further web, which further web is arranged parallel to the web or intersects the web.

6. A blade according to claim 1, further comprising:
at least another opening to provide a plurality of openings; and
a net or lattice of a plurality of webs which plurality of webs intersect one another or which plurality of webs have ends connected to one another, wherein each of the webs is arranged between two openings of the plurality of openings.

7. A blade according to claim 6, wherein the webs form a honeycomb structure defining the opening.

8. A blade according to claim 1, wherein a region of the blade or the entire blade is formed by webs, between which the opening or a plurality of openings are arranged.

9. A blade in accordance with claim 1, wherein:
said inclined flank increases a size of said opening from said tongue side to said palate side.

10. A laryngoscope comprising:
a blade comprising: a proximal end mechanically connected or connectable to a handle; a distal end an opening adjacent to the distal end, wherein the opening is arranged and configured in such a way that a view can be obtained, through the opening, from a side to be directed toward a patient's palate during an intended use of the blade to a side to be directed toward a base of the patient's tongue during the intended use of the blade, said opening having an inclined flank, the opening being arranged at least either distally in relation to a light exit face, through which illumination light exits during the intended use of the blade, or distally in relation to a light admission face, through which an image of the environment of the distal end of the blade can be captured during the intended use of the blade; and a handle connected to or connectable to the proximal end of the blade.

11. A laryngoscope according to claim 10, wherein the opening is not closed by a component made of an optically transparent material.

12. A laryngoscope according to claim 10, wherein the shape of the opening is adapted to the typical shape of the human epiglottis.

13. A laryngoscope according to claim 10, further comprising:
at least another opening to provide a plurality of openings; and
a web between two openings of the plurality of openings.

14. A laryngoscope according to claim 13, wherein the blade further comprises: a further web, which further web is arranged parallel to the web or intersects the web.

15. A laryngoscope according to claim 10, further comprising:
at least another opening to provide a plurality of openings; and
a net or lattice of a plurality of webs which plurality of webs intersect one another or which plurality of webs have ends connected to one another, wherein each of the webs is arranged between two openings of the plurality of openings.

16. A laryngoscope according to claim 15, wherein the webs form a honeycomb structure defining the opening.

17. A laryngoscope according to claim 10, wherein a region of the blade or an entirety of the blade is formed by webs, between which the opening or a plurality of openings are defined.

18. A laryngoscope blade comprising:
beam structure with a laryngoscope proximal end mechanically connected or connectable to a handle and a distal end, the beam structure defining an opening near the distal end of the beam structure, wherein the opening is arranged and configured to form a view passage from a tongue directed side of the beam structure, intended to face a patient's tongue during use, to a palate directed side of the beam structure, intended to face a patient's palate during use of the laryngoscope blade, said opening having an inclined flank; and
a hollow body extending from the proximal end over at least a portion of much of a length of the beam structure to a light exit face and a light admission face at a predetermined distance from the distal end of the beam structure, wherein the opening is arranged at least either distally in relation to the light exit face, through which illumination light exits during the intended use of the blade, or distally in relation to the light admission face, through which an image of the environment of the distal end of the blade can be captured during the intended use of the blade.

19. A laryngoscope blade according to claim 18, further comprising:
a joint connection disposed at or adjacent to the proximal end; and
a handle connected to or connectable to the proximal end of the blade via the joint connection.

20. A blade in accordance with claim 18, wherein:
said distal end of said hollow body is configured to receive a camera with a viewing field, said opening and said distal end of said hollow body being configured to arrange said opening in said viewing field.

* * * * *